United States Patent [19]

Flockhart et al.

[11] Patent Number: 5,298,256

[45] Date of Patent: Mar. 29, 1994

[54] DESMOPRESSIN BUCCAL PATCH COMPOSITION

[75] Inventors: Ian R. Flockhart, Cottingham, United Kingdom; Joseph H. Cort, Bad Krozingen, Fed. Rep. of Germany

[73] Assignee: Corint, Ltd., Geneva, Switzerland

[21] Appl. No.: 875,072

[22] Filed: Apr. 28, 1992

[51] Int. Cl.$^5$ ............................................. A61K 9/26
[52] U.S. Cl. ....................................... 424/435; 424/486
[58] Field of Search ................................. 424/435, 486

[56] References Cited

U.S. PATENT DOCUMENTS

| | | | |
|---|---|---|---|
| 4,764,378 | 8/1988 | Keith et al. | 424/487 |
| 5,135,752 | 8/1992 | Snipes | 424/435 |
| 5,139,790 | 8/1992 | Snipes | 424/435 |

*Primary Examiner*—Thurman K. Page
*Assistant Examiner*—Amy Hulina
*Attorney, Agent, or Firm*—Burgess, Ryan & Wayne

[57] ABSTRACT

A buccal patch is provided comprised of desmopressin and a matrix of a configuration and size as to fit into the buccal cavity and adhere to the oral mucosa so as to dispense desmopressin through transmucosal absorption into the bloodstream.

14 Claims, 4 Drawing Sheets

DESMOPRESSIN BUCCAL PATCH COMPOSITION

BACKGROUND OF THE INVENTION

1) Field of the Invention

The present invention relates, in general, to a novel pharmaceutical composition containing biologically-active desmopressin, a vasopressin-based oligopeptide, in combination with a matrix buccal patch. More particularly, the invention is generally concerned with a buccally-administered solid pharmaceutical composition containing various doses of the active component dispersed in a buccal patch matrix. The invention allows reproducible, patient-friendly administration of the drug even when the patient has nasal congestion since one usual mode of administration of desmopressin is by nasal drops or spray. The composition is well-tolerated by patients of all ages, is just a effective as when administered by nasal drops or spray, provides prolonged and reliable action and can be stored at room temperature.

2) Description of the Related Art

It has long been recognized that natural vasopressin has useful biological effects, such as antidiuresis, vasoconstriction of visceral blood flow and release of hematological clotting factors. Its utility, however, is limited by its short half-life as well as by its well-known systemic pressor effect which includes cardio-toxicity.

A variety of analogs of vasopressin have been synthesized in an effort to modify the properties of vasopressin and provide products having increased pharmaceutical utility. For example, vasopressin has been modified by desamination of cysteine in position 1 and replacement of arginine by its D-isomer at position 8 to yield desmopressin, hereinafter also referred to as "dDAVP". Desmopressin, which is immune to enzymatic cleavage as of the 1-2 and 8-9 C—N bonds, exhibits prolonged antidiuretic action and virtually no pressor action or cardio-toxicity. For example, see U.S. Pat. Nos. 3,497,491 and 4,235,881. In further modifications, the disulfide bridge has been replaced with a thioether linkage (—$CH_2S$— or —$SCH_2$—) or an ethylene (—($CH_2$—) linkage. See also U.S. Pat. No. 3,980,631.

These vasopressin-based oligopeptides have been administered by a variety of routes and in combination with a variety of pharmaceutical carriers and additives. For example, dDAVP has been administered intranasally, subcutaneously, intravenously and intramuscularly in physiological saline at pH 4.

Various attempts have also been made to effectively orally administer vasopressin-based oligopeptides, particular dDAVP. It has been traditionally accepted that such peptides are cleaved into inactive fragments in the gastrointestinal tract with little nonapeptide adsorption taking place. dDAVP has been incorporated in gelatin-based sub-lingual lozenges (A. Grossman et al. "Two new modes of desmopressin (dDAVP) administration", *British Medical Journal* May 17, 1980, 1215). A difficulty with sub-lingual lozenge is the necessity for the patient to restrain tongue movement so as not to swallow it and the fact that the sub-lingual salivary glands are very productive of secretion, which carries off a variable and unknown quantity of the drug to be swallowed.

Additionally, dDAVP has been formulated into an orally administered (swallowed) composition in the form of a tablet with various fillers and inert constituents. The effective claimed dosage would appear to be 100–200× the intravenous level, but a difficulty remains with all swallowed forms of oligopeptides—there will be a considerable patient-to-patient and day-to-day (in one and the same patient) variation in how much of the dosage is enzymatically cleaved and what fraction remains intact to be absorbed. Furthermore, if any such tablet or lozenge is gelatin-based, the water content will limit stability—thus, both the lozenges and the oral tablets are stored at 3°–8° C. Finally, the time-of-onset of any activity from a dose presented in the gut will vary from patient to patient and, in the same patient, from day to day.

It is known in the art that various chemical compositions can be administered to patients through the mucous membranes of the body. Suppositories for rectal/vaginal administration are well known as well as nasal sprays and drops. More recently, the patent literature has disclosed the administration of pharmaceutically active chemicals through the mucous membrane of the mouth. For example, in U.S. Pat. No. 4,764,378 which issued Aug. 16, 1988 to A. D. Keith et al. there is disclosed a buccal drug dose form for the transmucosal administration of drugs using an erodible matrix. A wide variety of other issued patents, both foreign and domestic are cited therein which pertain directly or indirectly to buccal drug dose forms and their methods of use. However, while the claims therein include heat-sensitive active substances such as Desmopressin, Calcitonin and Growth Hormone, no data has been presented therein, or elsewhere, that oligopeptides and protein hormones can survive the about 40° C. and one to two hour conditions used to include a drug in the given matrices. For Desmopressin no data has, to date, been presented at all. For Calcitonin and Growth Hormone the only data given are the approximate composition of the carrier mix and the statement that the latter hormones could be mixed therein, without mention of their chemical state and activity after mixing.

Accordingly, one or more of the following objects will be achieved by the practice of the present invention. It is an object of this invention to provide a pharmaceutical composition in the form of a buccal patch which contains biologically active desmopressin. A further object is to provide a composition in the form of a patch which is stable and can be stored at room temperature for extended periods of time. Another object of the present invention is to provide a method for administering desmopressin to a patient in need of such treatment and who at that time is experiencing nasal congestion. A still further object of the invention is to provide a method whereby desmopressin can be administered to a patient rapidly and in a manner which provides a sustained release of a continuous, even dosage over a period of time. These and other objects will readily become apparent to those skilled in the art in light of the teachings herein set forth.

SUMMARY OF THE INVENTION

In its broad aspect, the present invention is directed to a pharmaceutical composition in the form of a buccal patch containing a therapeutically effective amount of desmopressin which is stable in the dry state and therefore can be stored at room temperature. The invention is also directed to a process for the preparation of the pharmaceutical composition and its use in the treatment of a variety of conditions. In the process of accomplishing the above, comparisons have been made between a previously reported carrier composition (see U.S. Pat. No. 4,764,378) and the carrier composition which is described in British Patent Application, GB 9122765.2 filed October, 1991 by I. R. Flockhart et al.

DESCRIPTION OF THE PREFERRED EMBODIMENTS

Figure 1:
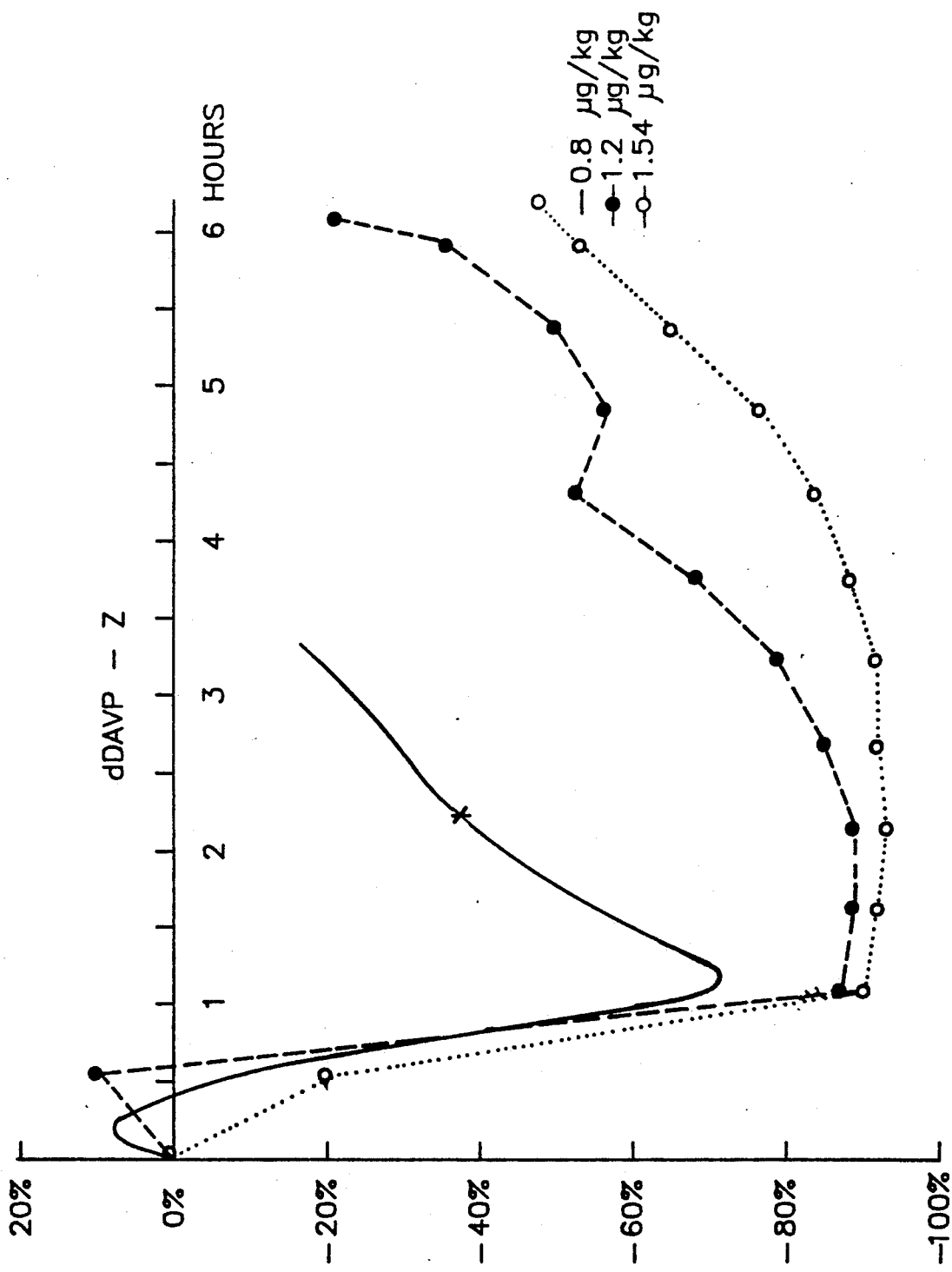
FIG. 1 is a graph depicting the antidiuretic changes for several buccal dosages (μg/kg) vs. time (hours) after dDAVP buccal administration in a carrier composition designated as "Z".

In view of the present invention, it has now been found possible to provide a novel pharmaceutical composition containing dDAVP, in dry form, on a matrix buccal patch which is stable, simple to insert, is hardly felt, dissolves within about 20 minutes, delivers its contained drug for absorption by the local mucous membrane, and can be stored at room temperature if access to moisture is prevented. In particular, it has been found to have a dose-related antidiuretic response in amplitude and particularly in duration ($T_{\frac{1}{2}}$), and total delivered activity (as measured by AUC) with the same or better degree of prolongation as that achieved by intranasal aqueous forms. The time of onset of the activity is short and predictable.

The invention thus improves patient compliance, particularly in the presence of nasal congestion with upper respiratory infections or in patients who need the drug following transsphenoidal surgery on the hypothalamus or pituitary. It can be used with advantage by patients with Diabetes insipidus, childhood enuresis and incontinence in general and all other approved and/or investigated uses of dDAVP, including all hematological uses. See P. M. Manucci, "DESMOPRESSIN: A Nontransfusional Hemostatic Agent", *Annual Review of Medicine* 4,1990, 55 and S. Reichlin, "The Neurohypophysis, Physiological and Clinical Aspects", *Plenum Medical Publ.* N.Y. 1984.

As indicated above, the pharmaceutical composition of the present invention is comprised of a matrix buccal patch containing desmopressin. Desmopressin, as previously indicated, is a peptide which can be represented by the following formula:

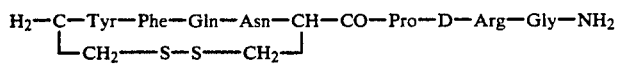

Although Desmopressin can be administered orally, it has been observed, as discussed above, that peptides are commonly cleaved in the gastrointestinal tract into inactive fragments and accordingly, little or erratic absorption of the intact peptide takes place. Accordingly, for many applications, dDAVP is usually administered intranasally, by nasal drops or sprays. However, in those instances where a patient has nasal congestion this particular route of administration is not desirable.

It has been found that dDAVP can be conveniently administered to a patient by means of a buccal patch wherein the active component is dispersed in a matrix, hereinafter also referred to as "Matrix F". The matrix is comprised of the following components in the indicated percentages by weight, based on the total weight of the matrix itself:

| Component | Weight % |
|---|---|
| a) Polyvinylpyrrolidone (mol. wt. 30,000) | 20–30 |
| b) Crodesta sucrose ester(s) | 0.1–3.0 |
| c) Propan 1,2-diol | 1–10 |
| d) $C_{12}$–$C_{18}$, alcohol such as Dodecanol, laurel or hexadecanol | 1–10 |
| e) PEG 1000 | 9–12 |
| f) PEG 1500 | 1–2 |
| g) PEG 4000 | 30–45 |
| h) PEG 8000 | 3–4 |
| j) Terpene ether, such as 1,8 cineole (eucalyptol) | 0.2–0.5 |

Each of the above components serves a definite function, as indicated below, in imparting the desired properties to the buccal patch matrix.

1. Low Dalton PEG's determine the consistency and melting pt. of the buccal patch and can range from 25 to 75%.

2. High Dalton PEG's and polyvinylpyrrolidone serve to further modulate the consistency of the patch and can range from 2 to 45%.

3. Crodesta sucrose ester is a sucrose cocoate ester (which can be replaced by Crodestas F10, F50, F110, F140 and F160) acts as an emulsifying and dispersing agent which are cleared as food additives.

4. Dodecanol/propan 1.2-diol is a combination of a fatty alcohol with either linear or branched chains (containing between 6 and 20 carbon atoms) with a di-hydroxylic alcohol (diol) (containing between 2 and 10 carbon atoms) which act, in combination with Crodesta, as penetration enhancers.

5. Cineole (a terpene ether which can be replaced by other similar molecules such as menthol, menthone, pulegone, etc.) may serve as a penetration co-enhancer but definitely serves as a taste masking device in the present case.

A particularly preferred formulation for the pharmaceutical composition of the present invention comprised of matrix F, is as follows:

| Component | Grams Used | Weight % |
|---|---|---|
| a) Polyvinylpyrrolidone (mol. wt. 30,000) | 2.75 | 27.3 |
| b) Crodesta sucrose ester(s) | 0.23 | 2.3 |
| c) Propan 1,2-diol | 0.47 | 4.7 |
| d) $C_{12}$–$C_{18}$, alcohol such as Dodecanol, laurel or hexadecanol | 0.32 | 3.2 |
| e) PEG 1000 | 0.95 | 9.4 |
| f) PEG 1500 | 1.04 | 1.0 |
| g) PEG 4000 | 3.82 | 38.0 |
| h) PEG 8000 | 0.38 | 3.8 |

| Component | Grams Used | Weight % |
|---|---|---|
| j) Terpene ether, such as 1,8 cineole (eucalyptol) | 0.050 | 0.5 |
| k) Desmopressin (dDAVP) | 0.050 | 0.5 |

In practice the compositions were prepared as follows:

Components a–f were melted gently together and stirred to produce an homogenous mass.

Components g–j were added to the above and melted together at a temp. not exceeding 80° C. The temp. was then allowed to decrease slowly with mechanical mixing until the temp. reached a value between 30° and 40° C., when (dDAVP) was added. This last procedure, only about 30 min. in duration, prevents heat inactivation of the peptide and is much shorter than the procedure used in Matrix Z.

The buccal patch can be prepared by a variety of methods and in several configurations known to those skilled in the art. Preferably, the buccal patch is in the form of a thin wafer or disk which can firmly adhere to the mouth mucosa and provide sufficient contact area so as to release Desmopressin quickly and in the desired amount.

The final buccal patch, preferably of an approximate size 7–10 mm×7–10 mm×1 mm, is a light but firm object when dry, and can be protected from moisture by presentation in a blister pack. It can easily be inserted between the gums and the cheek on either side, where it is hardly felt. There it absorbs heat from the mucosa to ensure slow melting and fluid from saliva to enable solution of the peptide. Within 10–30 mins. it melts and can no longer be felt, during which time the dose of peptide contained in the patch has been presented for absorption. The only restrictions on the patient are not to eat or drink during the melting time so as not to increase salivation and/or mechanically dislodge and swallow the patch.

The preferred concentration of Desmopressin in each individual buccal patch is from about 15 to about 250 μg, and more preferably from about 25 to about 100 μg.

A particularly desirable feature of the pharmaceutical compositions of the present invention is that they are stable at room temperature if protected from moisture. The shelf life of the buccal patches at room temperature is up to two years or more.

In order to demonstrate that the pharmaceutical composition of the present invention possesses superior properties to buccal patch compositions of the prior art, a comparison was made between a pharmaceutical composition comprised of the matrix F of the present invention and a pharmaceutical composition comprised of a matrix similar to that of the aforementioned U.S. Pat. No. 4,764,378, which also disclosed Desmopressin as an active component. This formulation was labelled "Matrix Z" and has the following composition:

| Component | % by Weight |
|---|---|
| Low Molecular weight polyethylene glycol (PEG), 100–4000 Daltons, (Melting Pt. 37° C.) | 20–75 |
| Medium to high mol. wt. PEG, 6,000 to 20,000 Daltons | 2–54 |
| Polyethylene oxide, mol. wt. 100,000 to 5,000,000 Daltons | 1–40 |
| Long chain saturated carboxylic acid (e.g. myristic acid) | about 4 |

In general, comparing Matrix F with Matrix Z there has been a shift to alcohols from long chain acids and the addition of Crodesta sucrose ester(s). The m.p. of F, like that of Z, is 37° C.

As will be noted by the antidiuretic assays reported in the Examples, regardless of dose, the action of the hormone analog starts in 30–45 minutes after insertion and reaches its peak activity within 60–90 minutes after insertion. The subsequent duration of activity is highly dose-dependent as shown in terms of mean $T_{\frac{1}{2}}$ values in hours:.

Figure 2:
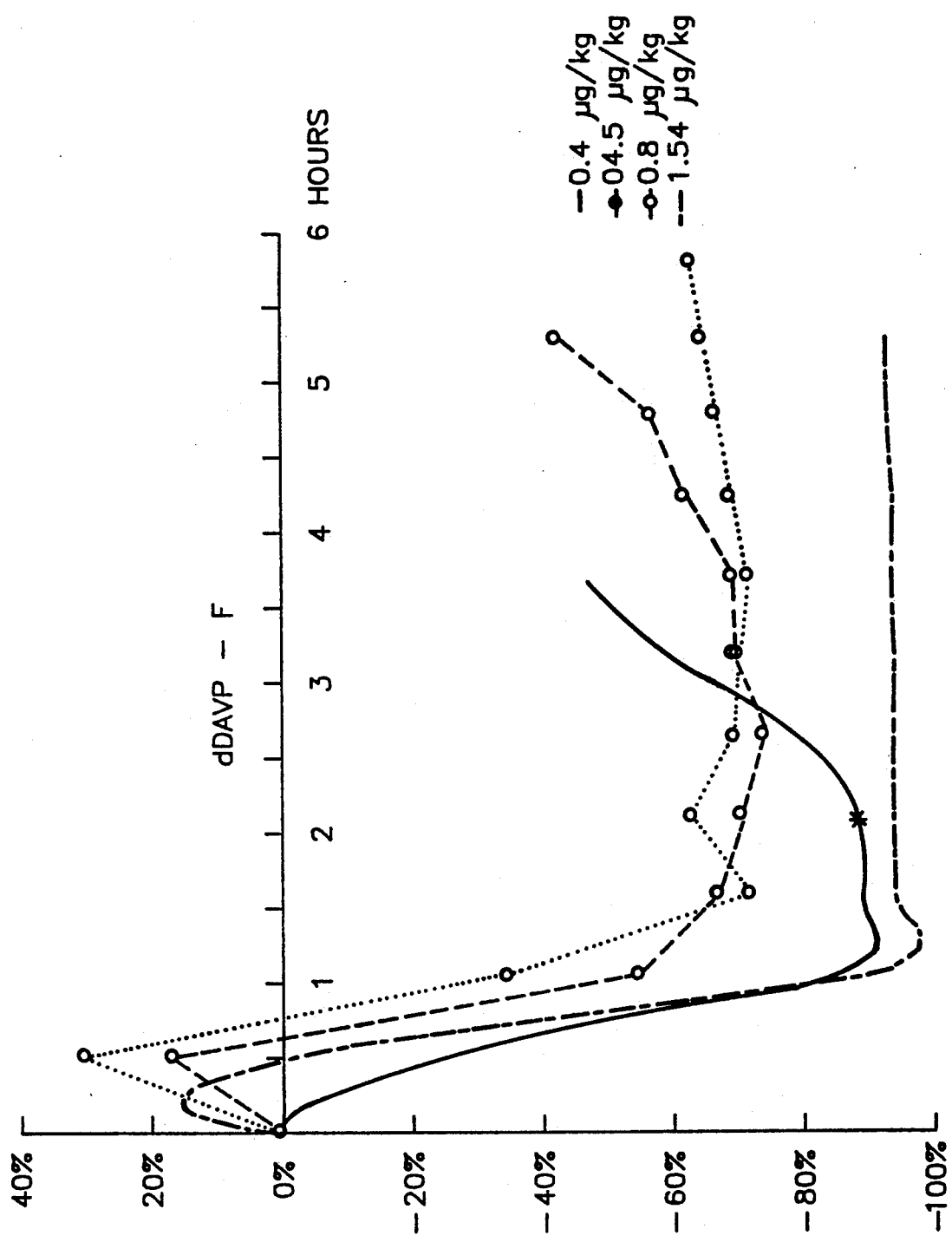
FIG. 2 is the same as FIG. 1, but with dDAVP incorporated in the carrier composition of the present invention, designated as "F".

| Dose | $T_{\frac{1}{2}}$ |
|---|---|
| In Matrix Z: see FIG. 1) | |
| 0.8 μg/kg | 1.7 |
| 1.2 | 5.0 |
| 1.54 | 8.0 |
| In Matrix F: see FIG. 2) | |
| 0.4 μg/kg | 3.5 |
| 0.45 | 5.0 |
| 0.9 | >7.5 |
| 1.54 | >12.0 |

All of the above times of onset and duration have been repeatedly seen in trained, human volunteers in a "Brattleboro Man" assay designed for dDAVP. See H. Nadvornikove et al., "A standardized desmopressin test of renal concentrating ability", *Clinical Nephrology*, 14, 1980, 142 and J. H. Cort et al., Role of the disulfide bridge and the C-terminal tripeptide in the antidiuretic action of vasopressin in man and the rat", *Kidney International* 8, 1975, 292.

Other comparative data is set forth in the examples and drawings.

The following examples are illustrative of the invention:

Buccal patches containing either 50 μg dDAVP/10 μmg (Z patches) or 100 μg dDAVP/100 mg (F patches) were used in a "Brattleboro Man" assay on human volunteers (n=6). All probands received both matrices on separate occasions. Between receipt and the first assay, the patches were stored at room temp. away from sunlight (brown plastic or glass coverings) for 2–4 weeks. By the time the last assay series was carried out, with dosage repetition for rough orientation on stability, the storage duration at room temperature had reached 4–12 weeks. Variation in dosage was achieved by cutting the tablets with a scalpel and weighing the fragments, or by using multiple fragments. The dosages, on a wt. basis, ranged from 0.4 to 1.54 μg/kg. The volunteers were trained and experienced with the assay technique, with 4 to 15 years of previous dDAVP-related assays carried out on them, so that each volunteer had a well-documented reference background of antidiuretic responses.

Each assay day started at 6:00–6:30 AM, after 8 hours of sleep. No food was allowed until the late evening of the same day, and no drugs at all were taken, including aspirin. None of the females were pre-menstrual on assay days. Each subject emptied his/her bladder and was then given 30 minutes to drink 1.5% of body wt. (measured) as lukewarm weak tea (3 bags/5 l.) very slightly sweetened with aspartame only. The excretory periods throughout were 30 minutes in duration. After 30 minutes, the volume of urine produced was measured and recorded and the same volume +30 ml. (to account for an average of 1 ml./min. insensible water loss—respiration and sweat—in a temperate climate) of the same tea was drunk. The water load is sufficient to suppress endogenous vasopressin secretion for that subject—the maintenance water loading kept the initial 1.5% dilution constant throughout the experiment. When two successive 30-minute periods showed the same rate of urine flow, the buccal matrix patches containing dDAVP were put in place. In the case of matrix F, blindly labelled blank patches, without dDAVP, were also made in the same manner and were tested. All the placebo blanks were without activity. Since maximum urine flow rates ranged from 11.0 to 18.0 ml/min (0.0035 ml./kg.min. to 0.01 ml/kg.min) the dDAVP-related decreases in urine flow rate were evaluated as (−) delta % flow-rate, counting down from 100% =max. pre-dDAVP flow rate. With matrix Z, three dosages were used: 0.8, 1.2 and 1.54 µg/kg. With matrix F, there also were three dosage ranges: about 0.4–0.45, 0.8 and about 1.6 µg/kg.

FIG. 1 gives the mean (−) delta % changes for the 3 buccal dosages in matrix Z vs. time (h.) after dDAVP buccal administration. Antidiuresis started by 30–45 minutes after administration in all cases, and peak antidiuresis was reached in all cases by 20–60 min. after administration.

FIG. 2 shows the same data as in FIG. 1 for the same probands, but this time the dDAVP was in matrix F. The principal difference between the responses was a dose-related $T_{\frac{1}{2}}$, with the F-matrix doses producing longer antidiuretic effects per dose than the Z-matrix doses.

Figure 3:
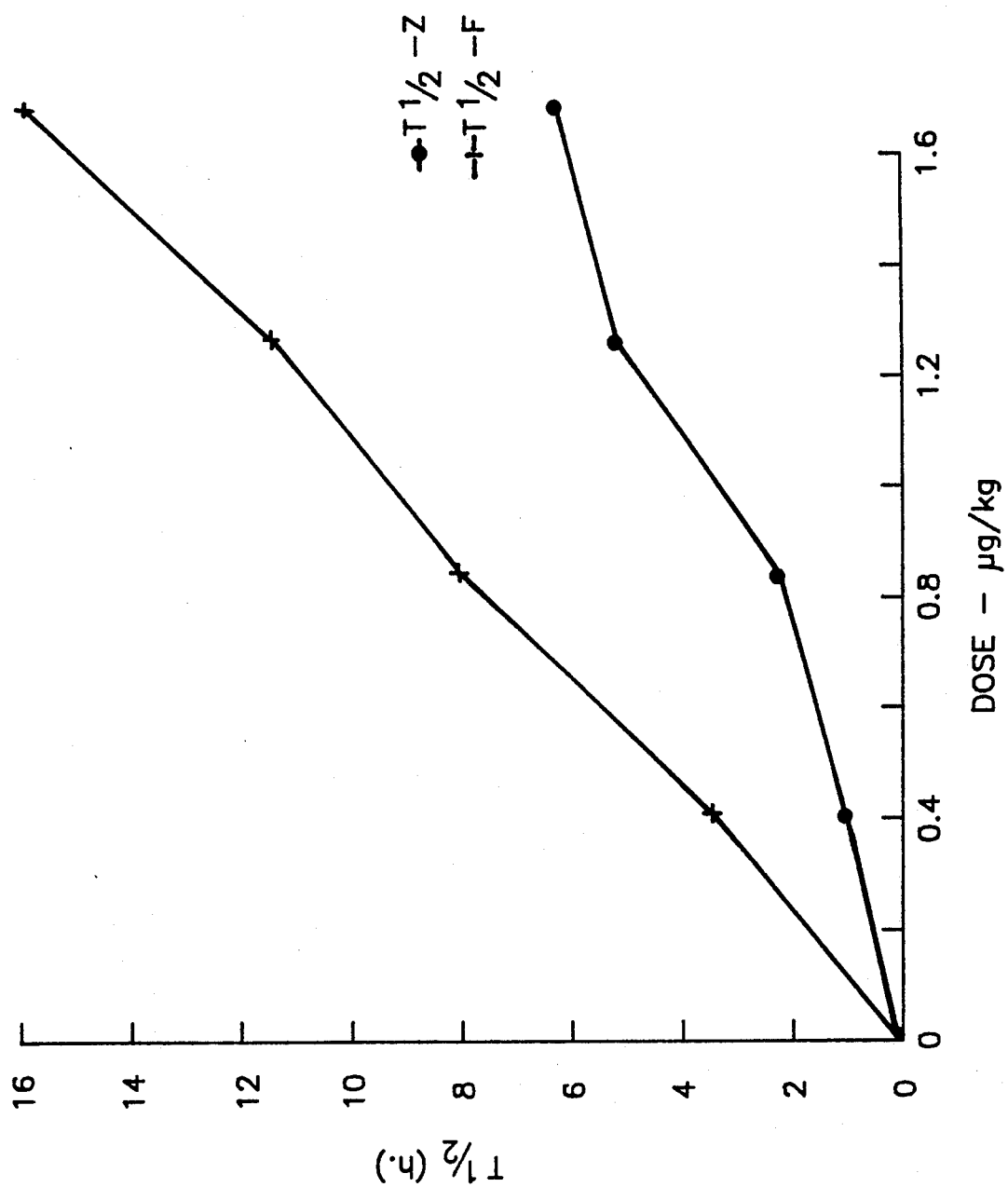
FIG. 3 is a graph depicting total dDAVP buccal dosage vs. mean $T_{\frac{1}{2}}$, comparing carrier Z and carrier F presentations.

FIG. 3 plots the $T_{\frac{1}{2}}$ data (h.) vs. dose for each of the two matrices separately. Taking $T_{\frac{1}{2}}$ as a measure of bio-availability, the F-matrix appeared to have delivered about twice the amount of dDAVP (all made from the same synthetic batch of raw material) as the Z-matrix material.

Figure 4:
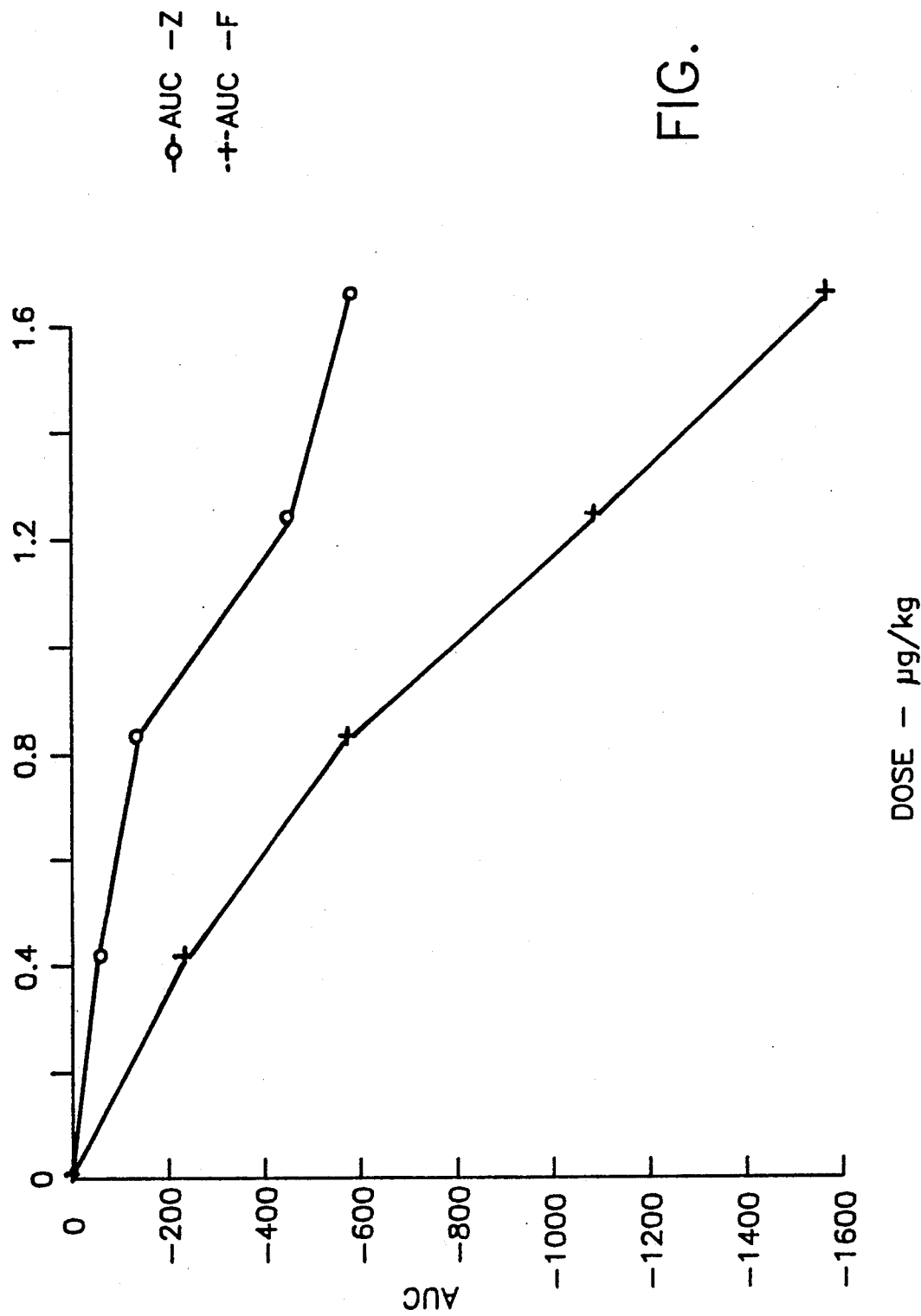
FIG. 4 is a graph depicting estimates of mean area under the curve (AUC) values of antidiuretic responses vs. total buccal dosage, comparing carrier Z with carrier F presentations, all of the above being data from the same group of probands.

FIG. 4 plots the area-under-the-curve (AUC) calculation of total delivered antidiuretic activity (here simplified to peak activity $\times T_{\frac{1}{2}}$) separately for the two matrices. Again, it would appear that the F-matrix delivered about twice as much antidiuretic activity as the Z-matrix material did.

Estimation of bio-availability in absolute % of administered dose absorbed and effective is very difficult only on the basis of one activity—antidiuresis—in a small group of probands. In general, it has been established that intranasal drops/spray get about 10% of the administered dose into the patient's circulation. The equivalent antidiuretic response to Z-matrix patches suggests that 7.5 to 10 times the dose must be given buccally as that given intranasally, i.e., the bio-availability would be 2–2.5% compared to i.v. administration. The apparent bio-availability of 5–7%, which from F-matrix buccal patches would then be about 5–7%, which approaches the efficiency of delivery from intranasal administration.

Thus, for F-matrix buccal patches, the preferred range of doses is from about 25 to about 50 µg/patch.

A drug formulation is not, however, evaluated by efficacy alone. Ordinary oral pills or sub lingual lozenges require 10–20 times the intranasal dose, but suffer from lack of patient to patient and day-to-day (in the sam patient) reliability and repeatability. Buccal patches can almost reach intranasal spray efficacy, but are even more reliable and repeatable than the intranasal formulations because they are independent of nasal congestion for whatever reason. Buccal patches can be kept at room temperature, which is a distinct advantage over all other dDAVP formulations, which require refrigeration at 3°–8° C.

While the present invention is directed primarily to buccal patches comprised of the F-matrix, the same formulation can be used for the preparation of suppositories. Suppositories comprised of the F-matrix formulations can contain one or more active components, such as desmopressin or other components such as calcitonin and the like.

Although the invention has been illustrated by the preceding examples, it is not to be construed as being limited to the indications related to the biological test, or to the materials employed therein. Rather, the invention is directed to the generic area as hereinbefore disclosed and should also cover other peptides such as Calcitonin and Growth Hormone. Various modifications and embodiments thereof can be made without departing from the spirit or scope thereof.

What is claimed is:

1. A pharmaceutical composition containing desmopressin as at least one of the active ingredients thereof, said composition being in the form of a buccal patch wherein the desmopressin is contained in an erodible matrix and of a configuration and size a to fit into the buccal cavity and adhere firmly to the mouth mucosa so as to disperse said desmopressin through transmucosal absorption into the bloodstream and wherein said matrix absorbs fluid from saliva and dissolves within about 20–30 minutes to thereby permit said desmopressin to reach its peak activity within 60–90 minutes after insertion of said buccal patch and thereafter provide a therapeutic level in the blood stream for a period of from 2 to 20 hours, as measured by its antidiuretic effect, and wherein said matrix consists essentially of the following composition:

| Component | Weight % |
| --- | --- |
| a) Polyvinylpyrrolidone (mol. wt. 30,000) | 20–30 |
| b) Crodesta sucrose ester(s) | 0.1–3.0 |
| c) Propan 1,2-diol | 1–10 |
| d) $C_{12}$-$C_{18}$, alcohol | 1–10 |
| e) PEG 1000 | 9–12 |
| f) PEG 1500 | 1–2 |
| g) PEG 4000 | 30–45 |
| h) PEG 8000 | 3–4 |
| j) Terpene ether, | 0.2–0.5. |

2. The pharmaceutical composition of claim 1 wherein an individual buccal patch contains from about 15 to about 250 µg of desmopressin.

3. The pharmaceutical composition of claim 1 wherein an individual buccal patch contains from about 25 to about 100 µg of desmopressin.

4. The pharmaceutical composition of claim 2 wherein an individual buccal patch is in the form of a disk.

5. The pharmaceutical composition of claim 1 wherein an individual buccal patch is in the form of a rectangle.

6. The pharmaceutical composition of claim 1 wherein an individual buccal patch is in the form of a square.

7. The pharmaceutical composition of claim 6 wherein the individual buccal patch has dimensions of approximately 7 mm×7 mm×1 mm.

8. A process for administering desmopressin to a patient in need of such treatment and whose condition is such as to necessitate avoidance of administration intranasally, said process comprising administering to said patient through the buccal mucosa, a pharmaceutical composition containing desmopressin as at least one of the active ingredients thereof, said composition being in the form of a buccal patch wherein the desmopressin is contained in an erodible matrix having the composition of claim 1 and of a configuration and size as to fit into the buccal cavity and adhere firmly to the mouth mucosa so as to disperse said desmopressin through transmucosal absorption into the bloodstream and wherein said matrix absorbs fluid from saliva and dissolves within about 20–30 minutes to thereby permit said desmopressin to reach its peak activity within 60–90 min. after insertion of said buccal patch and thereafter provide a useful therapeutic level in the bloodstream for a period of u to 20 hours.

9. The process of claim 8 wherein said buccal patch contains from about 15 to about 250 μg of desmopressin.

10. The process of claim 8 wherein said buccal patch contains from about 15 to about 100 μg of desmopressin.

11. The process of claim 8 wherein said patient is in need of treatment for a condition selected from the group consisting of diabetes insipidus, nocturnal enuresis, incontinence, urinary frequency, bleeding in hemophilia, von Willebrand's disease, liver cirrhosis, renal failure, assistance in improving contrast X-rays of the kidney.

12. A process for administering desmopressin to a patient in need of such treatment and whose condition is such as to necessitate avoidance of administration intranasally, said process comprising administering to said patient through the buccal mucosa, a pharmaceutical composition containing desmopressin as at least one of the active ingredients thereof, said composition being in an erodible matrix and of a configuration and size as to fit into the buccal cavity and adhere firmly to the buccal mucosa so as to disperse said desmopressin through transmucosal absorption into the bloodstream and wherein said matrix absorbs fluid from saliva and dissolves within about 20–30 minutes to thereby permit said desmopressin to reach its peak activity within 30–45 minutes of insertion of said buccal patch and thereafter provide a continuous therapeutic effect of from 5 to 20 hours, said erodible matrix having the composition of claim 1.

13. A process for the preparation of a pharmaceutical composition containing desmopressin as at least one of the active ingredients thereof which comprises melting the following first components in the indicated weight per cent and stirring to form a homogenous mass:

| Component | Weight % |
| --- | --- |
| a) Polyvinylpyrrolidone (mol. wt. 30,000) | 20–30 |
| b) Crodesta sucrose ester(s) | 0.1–3.0 |
| c) Propan 1,2-diol | 1–10 |
| d) $C_{12}$-$C_{18}$, alcohol | 1–10 |
| e) PEG 1000 | 9–12 |
| f) PEG 1500 | 1–2 | adding to said homogeneous mass the following second components and melting them together with said homogeneous mass at a temperature not exceeding 80° C.,

| Component | Weight % |
| --- | --- |
| g) PEG 4000 | 30–45 |
| h) PEG 8000 | 3–4 |
| j) Terpene ether | 0.2–0.5 | stirring said first and second components until the temperature is between about 30° to about 45° C., and then adding said Desmopressin.

14. The process of claim 13 wherein the pharmaceutical composition is further processed to form a buccal patch.

* * * * *